United States Patent
Nashwan

(10) Patent No.: US 7,681,578 B2
(45) Date of Patent: Mar. 23, 2010

(54) APPARATUS FOR TREATING PATIENTS SUFFERING FROM VASCULAR DISEASE BY MEANS OF INFRA-, AUDIBLE- AND ULTRASOUND WAVES

(76) Inventor: Khaled Awad Saleh Nashwan, Endresz Gyorgy U. 1/B, Pecs (HU) H-7633

( * ) Notice: Subject to any disclaimer, the term of this patent is extended or adjusted under 35 U.S.C. 154(b) by 1009 days.

(21) Appl. No.: 10/534,018

(22) PCT Filed: Nov. 5, 2003

(86) PCT No.: PCT/HU03/00091

§ 371 (c)(1),
(2), (4) Date: Nov. 21, 2005

(87) PCT Pub. No.: WO2004/041362

PCT Pub. Date: May 21, 2004

(65) Prior Publication Data

US 2006/0173234 A1    Aug. 3, 2006

(30) Foreign Application Priority Data

Nov. 5, 2002    (HU) .................................... 0203794

(51) Int. Cl.
*A61B 19/00* (2006.01)
(52) U.S. Cl. ........................ 128/898; 607/96
(58) Field of Classification Search ................. 601/1–4; 604/21, 22; 607/96, 98–102; 128/898
See application file for complete search history.

(56) References Cited

U.S. PATENT DOCUMENTS

| 4,069,467 A | * | 1/1978 | Burckhardt et al. ........... 367/93 |
| 4,305,014 A | * | 12/1981 | Borburgh et al. ............ 310/334 |
| 4,344,159 A | * | 8/1982 | Ballinger ..................... 367/87 |
| 4,628,573 A | * | 12/1986 | Hamada et al. ............ 29/25.35 |
| 5,050,588 A | * | 9/1991 | Grey et al. ..................... 601/4 |
| 5,509,896 A | * | 4/1996 | Carter ......................... 604/21 |
| 5,695,460 A | * | 12/1997 | Siegel et al. .................. 604/21 |
| 5,836,896 A | * | 11/1998 | Rosenschein .................. 601/2 |
| 5,853,005 A | * | 12/1998 | Scanlon ..................... 600/459 |
| 5,879,314 A | * | 3/1999 | Peterson et al. ................ 601/2 |
| 5,893,361 A |   | 4/1999 | Hughes |
| 6,126,619 A | * | 10/2000 | Peterson et al. ................ 601/2 |
| 6,558,330 B1 | * | 5/2003 | Ayter et al. ................. 600/459 |
| 6,575,956 B1 | * | 6/2003 | Brisken et al. .............. 604/500 |
| 6,790,187 B2 | * | 9/2004 | Thompson et al. ............. 601/2 |
| 7,273,458 B2 | * | 9/2007 | Prausnitz et al. ............... 601/2 |
| 2002/0091339 A1 |   | 7/2002 | Horzewski et al. |
| 2004/0048470 A1 | * | 3/2004 | Dinet et al. ................. 438/689 |

FOREIGN PATENT DOCUMENTS

| EP | 0 429 109 | 5/1991 |
| EP | 574923 A2 * | 12/1993 |
| EP | 1230951 A1 * | 8/2002 |
| GB | 2073593 | 10/1981 |
| WO | WO 9636286 A1 * | 11/1996 |
| WO | WO 9840016 | 9/1998 |
| WO | WO 0048518 | 8/2000 |
| WO | WO 0207667 | 1/2002 |

* cited by examiner

*Primary Examiner*—Ahmed M Farah
(74) *Attorney, Agent, or Firm*—Young & Thompson

(57) ABSTRACT

An apparatus (10) and a method for treating patients suffering from vascular disease with infra-, audible- and ultrasound waves. The apparatus (10) includes a treating head (15) for emitting sound waves with frequencies ranging from 1 Hz to 100 kHz and introducing the sound waves through a coupling medium (20) into a body portion (22) to be treated, an electronics (12) connected to the treating head (15) for energizing the treating head (15) to emit the sound waves, and a control panel (11) connected to the electronics (12) to choose the electronic waveform of the energizing.

8 Claims, 2 Drawing Sheets

APPARATUS FOR TREATING PATIENTS SUFFERING FROM VASCULAR DISEASE BY MEANS OF INFRA-, AUDIBLE- AND ULTRASOUND WAVES

FIELD OF THE INVENTION

The present invention relates to an apparatus and to a method and to a method capable of generating infra-, audible- and ultrasound waves, by means of which the treatment and curing of patients suffering from vascular disease can be accomplished via introducing sound waves generated in a given frequency range into the human system in an optimal manner. In particular, the apparatus according to the invention relates to the treatment/curing of diseases (for example vasoconstriction, decubitus, ischaemia, etc.) caused by circulatory deterioration.

BACKGROUND OF THE INVENTION

Diseases due to circulatory deterioration are amongst the most widespread diseases of developed societies. These can cause such organic, systemic and/or general complaints that can finally result in necrotizing the tissue involved, loosing the limb or a damage of the nervous system with its concomitant dreadful signs. If the organ involved is the heart itself, the circulatory deterioration can fall into a cardiac decompensation that leads to the death of the individual. Moreover, the formation of the mentioned diseases is a lingering process that takes several years or even decades and it is noticed by the individual only in the final stage when its symptoms intensify and become unbearable. Consequently, such an insidious disease is referred to here in case of which it would be of great importance nowadays to be treated cheaply and efficiently, to impede the deterioration in condition it causes and, in general, to prevent formation of the disease itself.

Presently there are several routes for conservative and semi-conservative treatment of vascular diseases already developed. The conservative therapy of peripheral vasoconstriction leading to complaints takes place medicinally which is fairly expensive and to various extent can also lead to the appearance of side-effects on people who were subjected thereto. In case of regional ischaemia of the skin and the skeletal muscles the application of various preparations, such as calcium channel blockers, can be effective. These preparations, however, act systemicly and can increase the local circulation only in that case when the ischaemia is acute and has got a functional origin, because in case of severe chronic ischaemia the arterioles are already maximally dilated. Their application is extremely dangerous, especially for people suffering from cardiac disease. Besides avoiding the dangerous side-effects there is a need for a compound of a specific effect for therapeutical use, especially for enhancing the circulation of the skeleton muscles in case of claudicatio intermittens, i.e. when during walk constriction of the arteries within the lower extremities causing ischaemia entails a spasm of pain in the calf, which pain ceases on stopping. Unfortunately, no such a specific compound has been discovered till now.

Amongst the medicaments used for therapy, at the moment the most well-known one is Pentoxifylline that is expansively used by physicians for the conservative treatment of vasoconstriction entailing the complaints. Its mechanism of action upon the circulation, however, differs from that of implied by the term 'vasodilator' widely known; according to our present scientific knowledge Pentoxifylline and compounds having similar action have got no proven effect upon vasoconstriction, that is, eventually upon the vessel wall itself. Pentoxifylline merely decreases rigidity of normocytes, corrects pathological deformations occurred in their shape, blocks thrombocyte aggregation, decreases viscosity of blood and hence increases the oxygen and nutrient supply of ischaemic tissues by means of improving the macro- and microcirculation. As a consequence, in case of proper reactions, circulation of the ischaemic tissue gets better and the colour of the skin changes: it passes from blue-grey to a healthy skin-coloured. The temperature of the ischaemic tissue is gradually increasing to that of the other intact portions, or at least approaches that. Depending on the extent of vasoconstriction, the pain eases or ceases altogether. Therefore, in view of the actual mechanism of action it would be more precise to classify Pentoxyfilline as a circulation enhancer.

In view of the above mechanism of action and by experience it is known that after giving up the application of circulation enhancers normocytes regain the rigidity they owned before the treatment and, as they are loosing their plasticity induced artificially by the medicament, a decrease in circulation due to vasoconstriction with its concomitant symptoms and complaints recurs. This means that the continued taking of preparations acting upon normocytes becomes necessary, besides taking into account neither the side-effects nor the effect gradually decreasing as a result of the long and frequent medicating.

However, Pentoxifylline and compounds having similar effects to that of Pentoxifylline do not affect the vessel-walls and their remarkable effect occurs, of course only in a short period of time, solely in case of frequent medicating; hence, neither further improvement of the ischaemic tissues can be accomplished nor the deterioration of the disease can be stopped by their usage.

Besides the medicinal therapy other treating techniques also exist and are used. U.S. Pat. No. 6,058,331 discloses an apparatus and a method for semi-conservative treatment of peripheral vascular disease and organ ischaemia. According to the given solution, the extent of blood flow in a patient's limb or ischaemic pain is measured by a suitable sensor and on basis of the obtained results a level of spinal cord stimulation or peripheral nerve stimulation is determined. Then in accordance with the level of stimulation determined the spinal cord, peripheral nerve or neural tissue ganglia is electrically stimulated by means of stimulation leads. The stimulation results in improving blood flow of the tissue and decreasing the ischaemic pain in the limb. The strength of the stimulation is continuously and automatically adjusted in accordance with the condition of the patient. A major drawback of this solution is that the implantation of the stimulation leads generally requires minor or major operations to be performed.

SUMMARY OF THE INVENTION

The aim of the present invention is to develop such a novel technique for treating diseases caused by circulatory deterioration and such an apparatus to carry out the treating technique itself, by means of which sound waves found to be the most effective for curing people suffering from vascular disease are introduced into the human body in an optimal way by exploiting simple laws of physics and without any kind of surgical action and with no need for medicinal therapy.

Our investigations led us to the conclusion that diseases due to circulatory deterioration can be effectively cured, or in a bad situation at least alleviated, by irradiating the patient's body with sound waves of frequencies chosen specifically. For this purpose sound waves with frequencies preferably between 1 Hz and 100,000 Hz, i.e. sound waves ranging from below the audible domain (i.e. infrasounds) through the audible domain up to the domain of ultrasounds are appropriate, wherein the majority of the sound waves are closer to the threshold frequency (about 16 Hz) of the audible spectrum by their application.

In one aspect, the present invention provides such an apparatus for treating patients suffering from vascular disease by means of a combination of infra-, audible- and ultrasound waves that comprises a treating head emitting sound waves with frequencies ranging from 1 Hz to 100 kHz and introducing these sound waves through a coupling medium into a body portion to be treated. The apparatus also comprises a suitable electronics connected to said treating head for energizing said treating head to emit said sound waves and a control panel connected to said electronics to choose the electronic waveform of the energizing. Furthermore, the apparatus according to the present invention optionally also comprises a heating device and a thermometer for measuring the temperature of the body portion to be treated, wherein the heating device and the thermometer are both connected to the electronics equipped with the control panel. From now on sound waves with frequencies ranging from 1 Hz to 100,000 Hz generated for treating purposes by the apparatus according to the invention will be referred to in brief as Parasound waves.

Waves emitted by the apparatus according to the invention fall in such energy density and frequency ranges that allow their penetration also into the deep-lying layers of the body portion to be treated. Hence they can act with a proper intensity on tissues, soft portions and bones within layers located in different depths, and as a result the aimed tissues, essentially the walls of muscle-type (generally medium-sized) arteries and that of smaller arteries are made to oscillate. Due to the massage of vessel-wall occurring as a result of the mentioned oscillation, the vessel-wall's own oxygen and nutrient supply is improving as a consequence of the enhanced diffusion due to the improvement in traversability of fenestration within the vessel-wall. Consequently, biological processes become active again, degeneration of cellular and fibrillar elements of the vessel-wall might slow down, stop or subside if they are yet in a reversible stage, elasticity of the arteries re-appears as the consequence of an increase (mainly due to a shift in the ratio of elastic fibers to collagen ones towards the elastic fibers) in the reproduction of the arteries' cellular and fibrillar elements. Furthermore, within tissues of insufficient circulation the smooth muscle cells and the endothelial cells of the arterioles, the smooth muscle cells, the pericytes and the endothelial cells of the capillaries of muscle and the endothelial cells of the actual capillary vessels regain their strength and size and return from the abiotrophic state into the normal thropic state. The collateral anastomosis formation stimulated by the pressure gradient due to an increased circulation in sane tissues increases oxygen and nutrient supply of the ischaemic tissues by means of improving the macro- and microcirculation. Furthermore, as the elements of the vessel-walls re-establish their activity and the blood vessels regain their elasticity, the circulation of blood within the ischaemic tissues returns to normal.

Preferably, the treating head is an electromagnetic or a piezoelectric tool and the treating head is equipped with a thermal sensor for controlling the heating device. Furthermore, the apparatus according to the present invention is also equipped with a pulsimeter for measuring the strength of the patient's pulse and preferably it has a visual display unit connected to the electronics.

In one of the preferred embodiments of the apparatus according to the present invention the treating head during a single treatment unit emits sound waves with frequencies continuously increasing within the period of 1 s to 200 s of the treatment unit from 1 Hz to 200 Hz at a rate of 1 Hz per seconds, then within the period of 200 s to 208 s of the treatment unit from 200 Hz to 1,000 Hz at a rate of 100 Hz per seconds, and finally within the period of 208 s to 307 s of the treatment unit from 1,000 Hz to 100,000 Hz at a rate of 1,000 Hz per seconds.

In another aspect, the present invention provides a method for treating patients suffering from vascular disease by means of a combination of infra-, audible- and ultrasound waves, wherein the method comprises the steps of providing an apparatus comprising a treating head emitting sound waves with frequencies ranging from 1 Hz to 100 kHz and introducing said sound waves into a patient's body portion to be treated, an electronics connected to said treating head for energizing said treating head to emit said sound waves, and a control panel connected to said electronics to choose the electronic waveform of the energizing; arranging a coupling medium on said body portion; bringing said treating head into contact with said coupling medium; chosing the waveform of the energizing; and applying said sound waves on said body portion via energizing said treating head by the electronics in accordance with the chosen waveform.

BRIEF DESCRIPTION OF THE DRAWINGS

The invention, its further advantages and characterizing features will be discussed in more detail with reference to the accompanied figures, wherein.

DETAILED DESCRIPTION OF THE PREFERRED EMBODIMENTS

Figure 1:
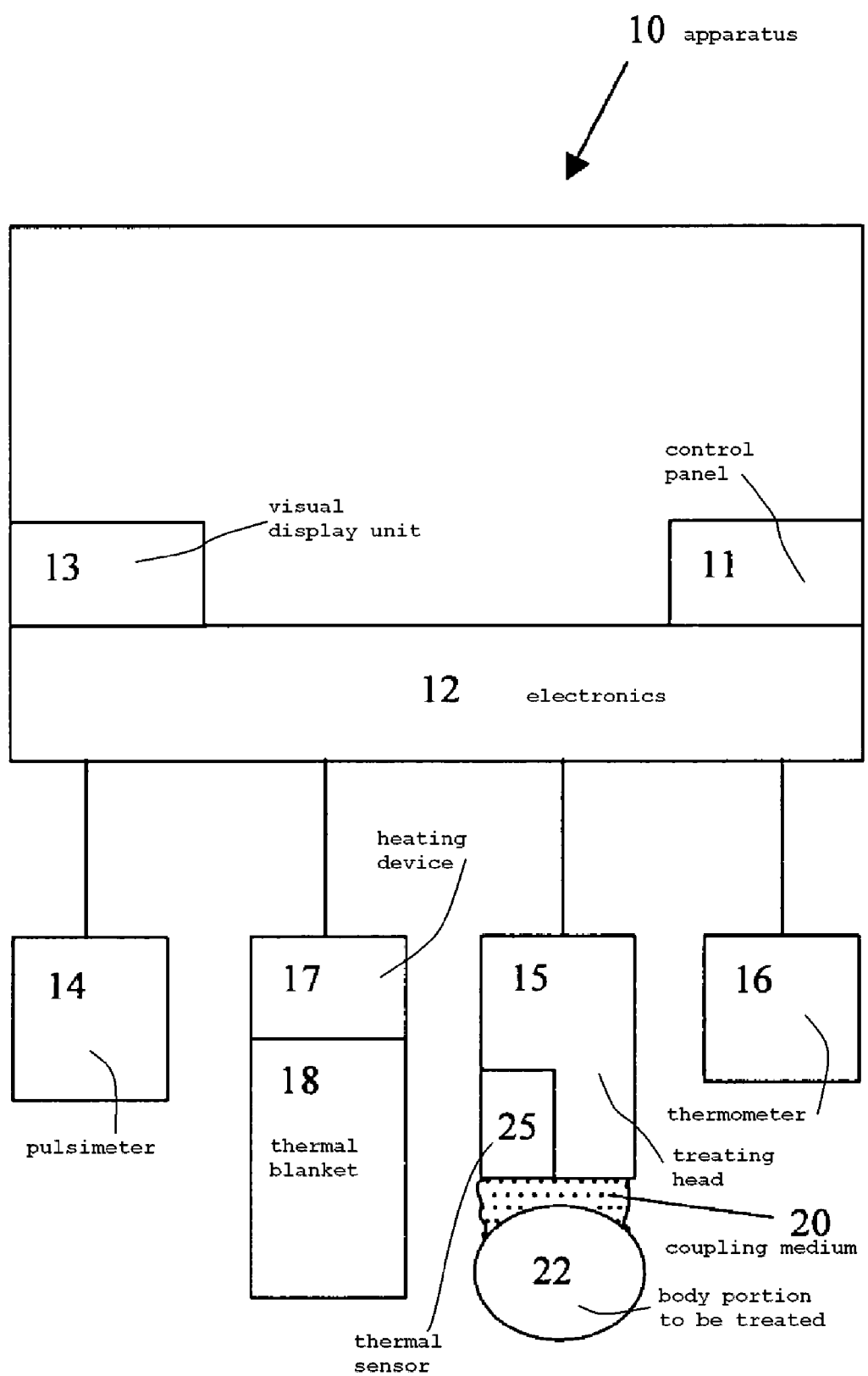
FIG. 1 shows a block diagram of one preferred embodiment of the apparatus according to the invention for treating people suffering from vascular disease; here the body portion to be treated is also illustrated symbolically.

Referring to FIG. 1, the apparatus 10 according to the invention comprises a control panel 11, an electronics 12, optionally equipped with a memory, that is preferably based on a printed circuit and allows proper operation of the apparatus 10, and a visual display unit 13, preferably in the form of an LCD display for displaying information. For its operation the apparatus 10 is connected via an electric connector (not shown in FIG. 1) to a current source, preferably to the power network. To accomplish data input, the control panel 11 is connected in a well-known manner to the electronics 12 and therethrough to the visual display unit 13. Furthermore, the apparatus 10 is also equipped with at least one treating head 15 for a treatment performed by the Parasound waves. The apparatus 10 also contains a heating device 17 for allowing an additional so-called hot chamber treatment to be carried out.

Treating head 15 is an essential part of the apparatus 10, it generates and emits Parasound waves corresponding to the electric waveform chosen by means of the control panel 11 and generated by the electronics 12. Considering its operation, the treating head 15 is basically a piezoelectric tool based on electromagnetic or inverse piezoelectric effect, however, it can also be prepared as such a tool which on the one hand is based on a different concept and on the other hand is capable of emitting Parasound waves within the given frequency range used for the treatment and of introducing those into a human body with an energy density of at most about 0.1 W/cm², preferably about 0.06 W/cm² in a manner to be detailed later.

Figure 2A:
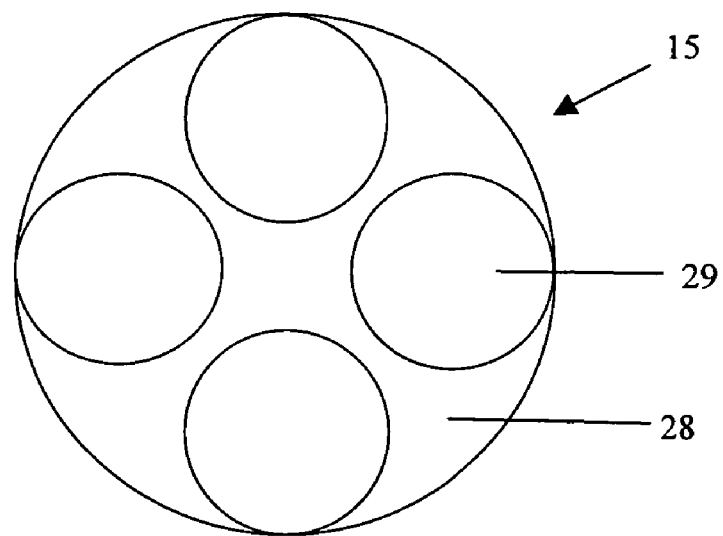
FIGS. 2A and 2B are the rear and front elevations, respectively, of a preferred embodiment of the treating head of the apparatus.
Figure 2B:
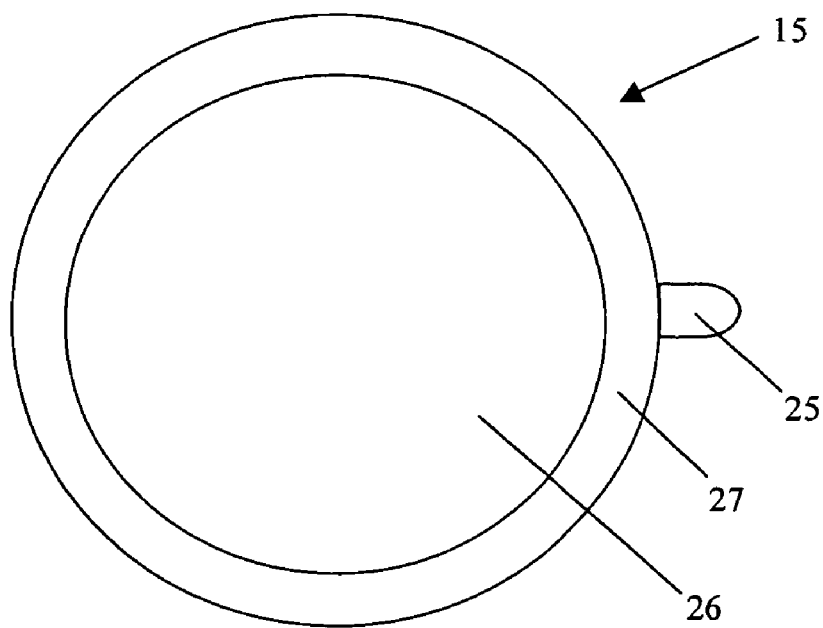

FIGS. 2A and 2B show in rear and front views, respectively, one possible embodiment of the treating head 15. According to this embodiment, the main portion of the treating head 15 is a base plate 28 having a metallic planar treating surface 26 embedded into a holder 27 which is preferably made of a plastic material. Base plate 28 is connected to the apparatus 10 via electric lead(s) (not shown in the drawing). Base plate 28 is preferably made of aluminium, however it can be prepared from any other material of good electric conductivity. In the present case the base plate 28 has a disc shape which is about 10 millimeters in thickness and about 65 millimeters in diameter. The outer diameter of the treating head 15 is about 75 millimeters. Base plate 28, however, can be formed with any shape, eg. With a shape that fits the body portion 22 to be treated in the best possible manner. Exciting means 29 generating the Parasound waves during the treatment in accordance with the waveform output by the electronics 12 are mounted onto the face of the base plate 28 opposite to the treating surface 26. The exciting means 29 of the embodiment of the treating head 15 at issue are cut away from a piezoelectric crystal with a suitable crystal axis orientation; hence, they emit the Parasound waves on basis of the inverse piezoelectric effect. The present embodiment of the treating head 15 preferably contains four exciting means 29. Preferably, the exciting means 29 also have a disc shape with a diameter of 25 millimeters. In general, exciting means 29 have such a shape and are arranged in such a geometry relative to each other that the frequency of the sound wave appearing as the superimposition of sound waves emitted by the exciting means 29 and to be fed into the body portion 22 to be treated could take any value within the interval ranging optionally from 1 Hz to 100,000 Hz. Accordingly, if eg. Four disc shaped exciting means 29 are used, these are arranged on the base plate 28 having also a disc shape in such a manner that (i) a single peripheral point of each exciting means 29 falls just on the contour of the base plate 28, (ii) the centers of the exciting means 29 define the vertices of a square that falls with its total area on the base plate 28, and finally (iii) the exciting means 29 do not abut each other. Obviously, by the application of more than four symmetrically arranged exciting means it is also possible to prepare a treating head that maximally satisfies the requirements of the therapy, i.e. which is capable of generating Parasound waves within just the desired frequency range.

One of the preferred embodiments of the treating head 15 is also equipped with a thermal sensor 25 which is connected to a control electronics responsible for the proper execution of the hot chamber treatment.

Heating device 17 forming part of the apparatus 10, in cooperation with the mentioned thermal sensor 25, is capable of a continuous or a periodic emission of hot air having the temperature of 25° C. to 50° C., preferably 30° C. to 45° C. under the control of an electronics (not shown in the drawing) that is integrated into the electronics 12 or is separated therefrom. A resilient tube-like thermal blanket 18 that receives the body portion 22 to be treated and is made of canvas or rubber-coated cloth with pores thereon is attached to the heating device 17. Its task is to adjust the temperature of the body portion 22 itself or its surface to a predetermined value and then to maintain this temperature before and/or during and/or after the treatment by the Parasound waves in certain cases, i.e. when the additional hot chamber treatment is also applied. As it can be seen from FIG. 1, the measurement of the temperature of the body portion 22 takes place preferably by an electronic thermometer 16 that is arranged on the body portion 22 and is also connected to the electronics 12 of the apparatus 10.

A further additional member of the apparatus 10 is a pulsimeter 14 for measuring the pulse strength of the patient under treatment. Values measured by the pulsimeter 14 connected to the electronics 12 can be displayed on its own display or on the visual display unit 13 of the apparatus 10 if the pulsimeter 14 lacks for that. Furthermore, measured values of the pulse strength, if desired, can be used for an automated control of the treatments carried out by the Parasound waves or optionally in combination with a hot chamber treatment.

One further part of the apparatus 10 is a software effectuating the control of the apparatus 10, which records and stores personal data related to the patient and/or data/information related to the course of the treatment (eg. settings related to the hot chamber treatment and to treatment by the Parasound waves) and values (of eg. body temperature, strength of the pulse) obtained during the treatment. Moreover, the mentioned software is responsible for carrying out the treatments on basis of the preset parameters or, in case of need, in a modified way with taking the actual measured values into account.

As it is well-known, the propagation velocity of sound depends slightly on the frequency and heavily on the density of the medium in which it propagates through. Infra-, audible- and ultrasound waves are almost totally reflected at a boundary between media of different acoustic impedances; assuming a perpendicular incidence of sound, the reflectance R can be calculated as $$R=[(q_1v_1-q_2v_2)/(q_1v_1+q_2v_2)]^2$$

wherein $q_1$ and $q_2$ denote the (volume) densities of the media, $v_1$ and $v_2$ stand for the propagation velocities within each of the media; furthermore, the acoustic impedance for a given medium is defined as a product of the density of the medium and the propagation velocity of sound in that medium. Generally, the acoustic impedances for liquid and solid media are generally much greater than for gases, so in case of a gas/liquid and a gas/solid boundary R≈1 holds, which means that at the incidence of sound, a crucial portion of the sound energy is reflected. Therefore, the energy of an infra-, audible or ultrasound can be transferred between solid objects arranged eg. in air by means of a so-called coupling medium that has a density almost equal to that of the solid objects and is inserted between the objects. During the propagation of a wave, the intensity of the wave decreases due to absorption and scattering. In general, the attenuation coefficient for shorter wavelengths is greater, consequently an ultrasound attenuates much faster than an audible one (eg. the absorption half-value thickness for a sound wave having a frequency of 10 kHz is about 100 meters in air and about 100 kilometres in water, while for an ultrasound having a frequency of 1 MHz it is about 1 m in air, several meters in water, about 2 centimeters in muscle tissues, while only a few millimeters in bones).

Accordingly, when it is required to introduce the Parasound waves by the treating head 15 of the apparatus 10 according to the invention into the tissues of a patient to be treated, the air gap between the treating head 15 and the body portion 22 to be treated should be filled up with a suitable coupling medium 20. The coupling medium 20 is preferably chosen to be a material in gelous state, such as commonly applied in ultrasonic diagnostic techniques. In case of appropriate construction of the treating head 15 and of the thermal blanket 18, water can also be used as the coupling medium 20.

In what follows the apparatus 10 according to the present invention is discussed in operation, i.e. during the treatment process of a patient suffering from a disease caused by a circulatory deterioration, eg. vasoconstriction.

Treatment of the patient by means of the treating head 15 is performed in treating cycles (called Parasound cycles) comprising predetermined treatment units (called Parasound units). Our studies suggested such a Parasound unit to be the most effective as for the treatment that is carried out in an automated manner more than once, has a total time length of 307 seconds and during which the treating head 15 emits sound waves of gradually increasing frequency from 1 Hz to 200 Hz at a rate of 1 Hz per second within the period of 1 s to 200 s thereof, then from 200 Hz to 1,000 Hz at a rate of 100 Hz per second within the period of 200 s to 208 s thereof, and from 1,000 Hz to 100,000 Hz at a rate of 1,000 Hz per second within the period of 208 s to 307 s thereof. In case of the above Parasound unit a single Parasound cycle preferably consists of six Parasound units repeated automatically and performed continuously after each other; hence it takes about half an hour to complete one Parasound cycle. Parasound cycles representing building blocks of the therapy, however, can differ from the one defined here; the number of the Parasound units involved therein and the actual sweepover in time and frequency within each Parasound units can be chosen arbitrarily. What is important is that the frequency of sound waves used for the treatment should always sweep over a frequency range falling between 1 Hz and 100 kHz within a predetermined period of time. Our studies revealed, however, that the above specially chosen sweepover in time and frequency repeated automatically provides an optimum effect of the vessel walls' massage due to Parasound waves fed into the patient.

The treatment of the patient starts on typifying in accordance with the classification of vasoconstriction. Based on this, one can determine the number of Parasound units required to treat the vasoconstriction concerned and the type and extent of possible additional treatments (eg. by means of a vasodilating cream, hot chamber treatment) to be optionally used in the given case. As for the treatment carried out by the apparatus 10 according to the invention, the classification of (acquired) vasoconstrictions according to Nashwan is as follows:
(i) vasoconstrictions leading to complaints even at rest or for small loads (active vasoconstrictions);
(ii) vasoconstrictions revealed by various tolerance tests or imaging (eg. ultrasonic, MRI, PET) techniques (latent vasoconstrictions); and
(iii) vasoconstrictions developing in certain cases as a consequence of the presence of predisposing factors, such as genetic factors, overweightness, obesity, strong smoking continued for years, diabetes mellitus, old age, etc. (potential vasoconstrictions).

Before starting on the treatment the number and the type of the Parasound units (i.e. the sweepover in time and frequency and the time and frequency ranges swept over) optimally required for treating the actual disease due to circulatory deterioration, specifically vasoconstriction are determined. Furthermore, at this stage it is also decided whether or not an additional hot chamber treatment should be applied. If a simultaneous hot chamber treatment is applied, after the patient had been at rest, eg. had laid on the treating bed, the resilient tube-like thermal blanket 18 is pulled on the body portion 22 to be treated, the pulsimeter 14 is attached to the patient in a suitable location and an electronic thermometer 16 is arranged on the body portion 22 to be treated. After the treatment unit had been chosen, parameters of the treating course (performed by the Parasound waves) and further in case of need the temperature of the heating device 17, its prospective change in time and the operation length of the heating device 17 are input into the apparatus 10 by means of the control panel 11. As a next step, the surface of the body portion 22 to be treated that receives the treating head 15 is thickly coated with the coupling medium 20 in gelous state, then the treating head 15 is accommodated to the body portion 22 in the given location without an air-gap and firmly affixed in this position. Then within the framework of the treating cycle sound waves of desired frequency and power are introduced by means of the apparatus 10 into the body portion 22 to be treated via running off the treating course set earlier that results in the massage of the vessel walls as already mentioned.

If a decision is made in favour of simultaneous hot chamber treatment, the heating device 17 is activated at the same time when introducing of the Parasound waves commences, and hence a given temperature is set within the thermal blanket 18. The temperature within the thermal blanket 18 is preferably increased in every Parasound unit by a given value, preferably by at most 3° C. until the predetermined temperature value is reached. Our experience shows that the temperature within the thermal blanket 18 can be raised at most 45° C. without the appearance of a decrease in the effectiveness of the treatment and without cease of the patient's comfort.

The importance of the additional hot chamber treatment occurs in the enhancement of a reflexlike dilation of blood vessels contracted as a consequence of the cool skin which occurs due to the circulatory deterioration, and hence it improves the effects and the efficiency of the therapy with the Parasound waves. Circulatory deterioration results in cooling of the skin which elicites a reflexlike contraction of the blood vessels. This consequently further lowers the temperature of the skin that is already cold and excarbates the complaints originating therefrom. In this way the process as a whole changes into a circulus vitiosus, which means such a chain of processes wherein a newly occurred element puts in action reaction(s) further exacerbating actual complaints. It is exactly this process getting worse that the hot chamber treatment interrupts.

We note here that the hot chamber treatment is of great importance in case of acute or functional ischaemia as in case of chronic ischaemia the arterioles are already maximally dilated. We also note here that for impalpable popliteal artery the hot chamber treatment should be used only with great caution as an increase in the temperature of the skin results in an increased energy requirement and in case of severe ischaemia the formation of gangraena might accelerate.

Summarized in brief: the apparatus of the present invention serves to treat diseases (for example vasoconstriction, decubitus, ischaemia, etc.) caused by circulatory deterioration and to prevent the formation thereof. The Parasound waves emitted by it, because of their specific character, can be effectively used, however, in other fields too, eg. to treat people suffering from lumbago or neuralgia or also to prevent the formation thereof.

It is understood by those skilled in the art that the apparatus according to the invention and its treating head can have numerous modifications and variations that can be accomplished without departing from the spirit and scope of the invention as set forth in the following claims.

The invention claimed is:
1. A method for treating patients suffering from vascular disease by a combination of infra-, audible- and ultrasound waves, wherein said method comprises the steps of
providing an apparatus comprising:

a treating head emitting sound waves with frequencies lying within an operation range extending from a lower limit of 1 Hz to an upper limit of 100 kHz, an electronics connected to said treating head for energizing said treating head to emit said sound waves, wherein the sound waves emitted by said treating head constitute a treatment unit of a predetermined total length in time;

the frequencies of the sound waves within said treatment unit sweep over the operation range from said lower limit to said upper limit in given steps, said steps changing in length over time during said treatment unit; and each sound wave of a certain frequency is emitted for a given period of time, said periods of time adding up to the total length in time of the treatment unit;

arranging a coupling medium on a patient's body portion to be treated;

bringing said treating head into contact with said coupling medium;

energizing said treating head to emit said sound waves through the coupling medium and into the body portion to be treated.

2. The treating method according to claim 1, wherein said treatment unit is chosen in such a way that the treating head emits sound waves of certain frequencies, the frequency continuously increasing from 1 Hz to 200 Hz at a rate of 1 Hz per seconds within the period of 1 s to 200 s thereof, then from 200 Hz to 1,000 Hz at a rate of 100 Hz per seconds within the period of 200 s to 208 s thereof, and finally from 1,000 Hz to 100,000 Hz at a rate of 1,000 Hz per seconds within the period of 208 s to 307 s thereof.

3. The treating method according to claim 2, wherein said treatment unit is performed more than once.

4. The treating method according to claim 2, wherein each sound wave of a certain frequency is emitted by the treating head with an energy density of at most 0.06 W/cm$^2$.

5. The treating method according to claim 1, wherein:

there is further provided a heating device connected to said electronics, said heating device being attached to a resilient thermal blanket being capable of receiving the body portion to be treated;

arranging said body portion within said thermal blanket; and generating a controlled amount of heat within said thermal blanket by said heating device and performing thereby a simultaneous hot chamber treatment of said body portion.

6. The treating method according to claim 5, further performing said hot chamber treatment of said body portion at a preset temperature falling between 25° C. and 50° C., preferably between 30° C. and 45° C.

7. The treating method according to claim 6, wherein the preset temperature is between 30° C. and 45° C.

8. The treating method according to claim 1, wherein each sound wave of a certain frequency is emitted by the treating head with an energy density of at most 0.06 W/cm$^2$.

* * * * *